(12) United States Patent
Pertile

(10) Patent No.: US 8,466,112 B2
(45) Date of Patent: Jun. 18, 2013

(54) COMPOSITIONS COMPRISING ORNITHINE KETOGLUTARATE (OKG)

(75) Inventor: Paolo Pertile, San Pietro Vlminario (IT)

(73) Assignee: Cutech S.r.l., Padua (IT)

( * ) Notice: Subject to any disclaimer, the term of this patent is extended or adjusted under 35 U.S.C. 154(b) by 503 days.

(21) Appl. No.: 12/676,774

(22) PCT Filed: Sep. 2, 2008

(86) PCT No.: PCT/EP2008/007143
§ 371 (c)(1),
(2), (4) Date: Mar. 5, 2010

(87) PCT Pub. No.: WO2009/030453
PCT Pub. Date: Mar. 12, 2009

(65) Prior Publication Data
US 2010/0249041 A1    Sep. 30, 2010

(30) Foreign Application Priority Data
Sep. 7, 2007  (EP) .................................... 07017538

(51) Int. Cl.
*A61K 38/00* (2006.01)
*A61P 17/14* (2006.01)

(52) U.S. Cl.
USPC ........................................................ 514/20.7

(58) Field of Classification Search
None
See application file for complete search history.

(56) References Cited

U.S. PATENT DOCUMENTS

2003/0143311 A1   7/2003   Gillota
2005/0090545 A1   4/2005   Leitman

FOREIGN PATENT DOCUMENTS

| CN | 1709523 A | 12/2005 |
| WO | 91/18610 A | 12/1991 |
| WO | 94/09750 A | 5/1994 |
| WO | 2004/026259 A | 4/2004 |

OTHER PUBLICATIONS

Burke. Annals of Surgery, 1981, 194(4), 413-427.*

* cited by examiner

*Primary Examiner* — Noble Jarrell
(74) *Attorney, Agent, or Firm* — Dilworth & Barrese, LLP.

(57) ABSTRACT

Suggested are new compositions comprising Ornithine Ketoglutarate (OKG) and a cosmetically acceptable carrier the latter selected from the group consisting of aliphatic alcohols or polyols having 2 to 15 carbon atoms or oil bodies.

7 Claims, No Drawings

COMPOSITIONS COMPRISING ORNITHINE KETOGLUTARATE (OKG)

FIELD OF THE INVENTION

The present invention is related to compositions comprising Ornithine Ketoglutarate, their use for making cosmetic compositions and/or medicaments for fighting various diseases associated with disorders of hair follicles as well as a process for curing said diseases and disorders by use of OKG.

BACKGROUND OF THE INVENTION

It is well known from the state of the art that life of a hair follicle is characterized by continual and cyclical transition between a growth stage of the follicle (anagen) in which, amongst other things, the development of the hair is observed (by virtue of the activity of the keratinocytes), a subsequent regression stage (catagen) in which the programmed death (apoptosis) of a considerable portion of the cells of the follicle takes place, and a third, quiescence stage (telogen) at the end of which the hair follicle returns to the anagen stage with the formation of a new hair shaft.

The duration of the various stages of the life cycle of the hair follicle depends substantially on its position on the body. For example, whereas in the scalp region, anagen lasts from two to eight years, compared with a period of a few weeks for the catagen stage and a few months for the telogen stage, in the eyebrow region, the anagen stage lasts for only a few months. This time ratio also determines the percentage of hair follicles which are present, on average, in the various stages of the cycle, for each region of the body. The durations of the various stages of the cycle, as well as the transition between one stage and another are regulated by complex biological interactions, the mechanisms of which are not entirely clear, between the various parts of the hair follicle and between the follicle and the surrounding epithelial environment. It is, however, known that these stages are affected by many endogenous and exogenous factors which act, directly or indirectly, on the hair follicle to lengthen or shorten the duration of each stage.

Many attempts have been made to identify factors causing an early entry into the catagen phase or disorders of the hair follicle and to provide actives for fighting these symptoms, however, with little success so far. It is believed that an active promoting hair growth and in particular being truly successful against hair loss would double the existing market for men's hair care products world-wide.

In this context reference is made to WO 94/09750 A1 (Unilever) disclosing a composition comprising (a) ornithine, its salts, hydrosalts and precursors and (b) cosmetically acceptable carrier. As set out in the specification (page 9) typical examples for suitable derivatives of ornithine are ornithine hydrochloride, L-cystinylornithine, L-ornitylcitrulline and the like. According to the teaching of the application the compositions are used topically to the bald or balding scalp in order to promote hair growth. However, the technical teaching of the document relates to the urea cycle, including its intermediate molecules, such as ornithine. The application neither teaches nor suggests the use of alpha-ketoglutarate or the combination of both ornithine and alpha-ketoglutarate.

More particularly, the concrete problem underlying the present invention has been to increase the anagen period of the hair follicles and to delay the decline of the catagen phase to provide hair follicles more time to grow. At the same time growth of the hair follicles should be stimulated along with an increase of the number of cells in the proliferative stage. Finally, the new compositions should avoid any increase in cell apoptosis.

DETAILED DESCRIPTION OF THE INVENTION

The present invention refers to compositions comprising Ornithine Ketoglutarate (OKG) and a cosmetically acceptable carrier; the latter selected from the group consisting of aliphatic alcohols or polyols having 2 to 15 carbon atoms or oil bodies.

Surprisingly it has been observed that Ornithine Ketoglutarate strongly increases hair follicle growth. At the same time OKG delay the decline of the catagen phase and enlarges the anagen phase during which the growth of the hair follicles can take place. Finally, the numbers of apoptotic cells are significantly decreased, while cell proliferation remains at the same level. The conclusion of these results, which are supported by experimental data in detail, is that OKG represents a rather effective active agent for fighting many kinds of diseases associated with disorders of hair follicles including those types of skin diseases which are mediated by disorders or diseases of hair follicles. In addition, OKG may be also useful in the preparation of artificial skin.

It has been found that OKG shows the highest activity at a working concentration of about 0.01% by weight (b.w.) to about 1% b.w., preferably about 0.05% b.w. to about 0.1% b.w.—all calculated on the total cultivation medium. Of course, also at lower concentrations OKG shows some effects, however usually the results are less significant. Higher concentration may work as well, but usually do not lead to better results.

Ornithine Ketoglutarate (OKG)

Ornithine (alpha-) ketoglutarate, abbreviated OKG, also known as ornithine 2-oxoglutarate or ornithine oxoglutarate (OGO), is a salt formed of two molecules of the non-protein amino acid, L-ornithine, and one molecule of the Krebs cycle dicarboxylic acid, alpha-ketoglutarate.

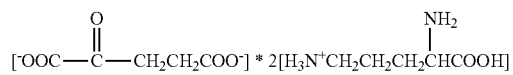

OKG has been used both enterally and parenterally in burn, trauma, surgical and chronically malnourished patients. It appears to decrease protein catabolism and/or increase protein synthesis under these conditions. OKG is a popular nutritional supplement for athletes, among others. The actions of OKG can be attributed to the metabolites that the OKG components, L-ornithine and alpha-ketoglutarate, give rise to. These metabolites are L-arginine, L-glutamine, L-proline and polyamines. The metabolism of L-glutamine and L-arginine is altered in trauma, and this alteration is linked to immune dysfunction. One of the major biochemical events that occurs following a burn injury is a fall in intramuscular L-glutamine. This amino acid is released from muscle tissue to meet the increased needs of other cells, in particular immune cells and intestinal cells. L-glutamine is now known to be essential for sustaining the proliferation and activation of immune cells. In the intestine it is essential for maintaining the integrity of the mucosal barrier and its metabolic and immune function. Immune and gastrointestinal dysfunctions occur when de novo L-glutamine synthesis is insufficient to maintain normal function of immune cells and enterocytes.

In this context reference is made to WO 06/075924 A1 (SGP AND SONS AB) which is related to the problem of antineoplastic preparation. The essence of the solution is that the preparation contains inter alia alpha-ketoglutarate of ornithine. The application discloses the ability of OKG and related compounds to stimulate the proliferation of A 549 cells.

Cosmetically Acceptable Carriers

In the context of the present invention cosmetically acceptable carrier can be chosen from aliphatic alcohols or polyols having 2 to 15 carbon atoms or oil bodies.

Alcohols and Polyols

Ethanol, isopropyl alcohol or polyols, may be used as cosmetically acceptable carriers. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Oil Bodies

Suitable oil bodies, forming cosmetically acceptable carriers, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils.

Usually the cosmetic compositions contain about 0.1 to about 15, preferably about 1 to about 10 and more preferably about 2 to about 5% b.w. OKG, while the remaining part represents the carrier.

INDUSTRIAL APPLICATION

Another object of the present invention is related to the use of OKG for making cosmetic compositions, in particular hair care compositions.

Further objects of the present invention concern the use of OKG for making a medicament for influencing the metabolism of hair follicles and the modulation of their vital cycle;
for treating disorders of hair follicles, in particular hair loss;
for treating diseases of hair growth; and
for treating skin diseases or disorders mediated by hair follicle metabolism.

Finally, the present invention also concerns a process for the cosmetic treatment of disorders of hair follicles, diseases of hair growth and skin diseases or disorders mediated by hair follicle metabolism, which is characterised in that OKG is administered either by oral or topical application to hair or skin.

The administration of the OKG can be topical or oral. In case of topical application all kinds of compositions are possible: lotions, creams, emulsions and the like. For oral uptake capsules are the preferred galenic forms. These embodiments are explained below in more detail.

Capsules and Microcapsules

For oral uptake encapsulation of the compositions represents a preferred embodiment. Usually encapsulation can take place by using gelatine as a matrix. It is also possible to prepare capsules by adding a gelling agent like e.g. alginate to the OKG composition and drop the mixture into a bath of a calcium salt. Both methods lead to macrocapsules having a diameter of about 1 cm to about 5 cm which are toxicologically safe and suitable for consumption.

It may also be desirous to encapsulate the OKG for the formulation of compositions which are developed for topical application. This can have different reasons: stabilisation against interaction with other compounds in the formulation, protection against chemical degradation or simply for preparing a very aesthetical product. For this purpose usually microcapsules are applied. "Microcapsules" are understood to be spherical aggregates with a diameter of about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agamo rose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone. Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

Artificial Skin

Another object of the present invention is the use of OKG for making artificial skin. Usually, the possible approaches for tissue engineering in general and the use of artificial skin in particular fall into the following three categories:

Epidermal replacements—consisting of keratinocytes grown either alone (on the surface of a tissue culture flask), or in close association with a carrier vehicle such as a polymeric film or bio-resorbable matrix.

Dermal replacements—consisting of a support structure able to support the infiltration, adherence, proliferation and neo-matrix production by fibroblasts (and in some cases endothelial cells).

Skin substitutes—are a combination of the above, able to support both dermal and epidermal components.

At present two methods are well established for the formation on artificial skin:

Mesh Scaffolding Method

According to the MS method fibroblasts are transferred from the vials into roller bottles, which resemble liter soda bottles. The bottles are rotated on their sides for three to four weeks. The rolling action allows the circulation of oxygen, essential to the growth process. Subsequently the cells are removed from the roller bottles, combined with a nutrient-rich media, flowed through tubes into thin, cassette-like bioreactors housing the biodegradable mesh scaffolding, and sterilized with e-beam radiation. As the cells flow into the cassettes, they adhere to the mesh and begin to grow. The cells are flowed back and forth for three to four weeks. Each day, leftover cell suspension is removed and fresh nutrient is added. Oxygen, pH, nutrient flow, and temperature are controlled by the culture system. As the new cells create a layer of dermal skin, the polymer disintegrates. Finally, when cell growth on the mesh is completed, the tissue is rinsed with more nutrient-rich media. A cryoprotectant is added. Cassettes are stored individually, labelled, and frozen.

Collagen Method

Using collagen as the raw material for making the artificial skin in the first step cells are transferred to a culture system. A small amount of the cold collagen and nutrient media, approximately 12% of the combined solution, is added to the fibroblasts. The mixture is dispensed into molds and allowed to come to room temperature. As the collagen warms, it gels, trapping the fibroblasts and generating the growth of new skin cells. About two weeks after the collagen is added to the fibroblasts, the extracted keratinocytes are thawed and seeded onto the new dermal skin. They are allowed to grow for several days and then exposed to air, inducing the keratinocytes to form epidermal layers. Finally, the new skin is stored in sterile containers until needed.

The preparation of artificial skin containing hair follicles belongs to the state of the art; a suitable process is disclosed, for example, in the Chinese patent application CN 170523 A1. Although these technologies are presently providing some results on animal models only, it is clear that human hair follicle cultures included in artificial skin tissues could be achievable in a relatively short span of time. These new technologies will require the setting up of appropriate culture media, suitable to support the metabolic requirements of both artificial skin cells, hair follicle cells and/or the hair follicle. On this regards, the composition of these culture media would take great advantage from the addition of OKG, in reason of its stimulant action on hair follicle metabolism and the modulatory effect on its cycle.

Cosmetic Compositions

The cosmetic compositions according to the present invention, preferably compositions for the treatment of human hair, may contain additional compounds like for example surfactants, oil bodies, emulsifiers, superfatting agents, pearlising waxes, consistency factors, polymers, silicone compounds, waxes, stabilizers, antidandruff agents, biogenic agents, film formers, preservatives, perfume oils, dyes and the like as additional auxiliaries and additives.

Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaints. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies are those which have already been compiled among the suitable cosmetic carriers.

Emulsifiers

Other surfactants may also be added to the preparations as emulsifiers, including for example:
- products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
- $C_{12/18}$ fatty acid monoesters and diesters of addition products of 1 to 30 mol ethylene oxide onto glycerol;
- glycerol mono- and diesters and sorbitan mono- and diesters of saturated and unsaturated fatty acids containing 6 to 22 carbon atoms and ethylene oxide addition products thereof;
- addition products of 15 to 60 mol ethylene oxide onto castor oil and/or hydrogenated castor oil;
- polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
- addition products of 2 to 15 mol ethylene oxide onto castor oil and/or hydrogenated castor oil;
- partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
- mono-, di and trialkyl phosphates and mono-, di- and/or tri-PEG-alkyl phosphates and salts thereof;
- wool wax alcohols;
- polysiloxane/polyalkyl polyether copolymers and corresponding derivatives;
- mixed esters of pentaerythritol, fatty acids, citric acid and fatty alcohol and/or mixed esters of $C_{6-22}$ fatty acids, methyl glucose and polyols, preferably glycerol or polyglycerol,
- polyalkylene glycols and
- glycerol carbonate.

The addition products of ethylene oxide and/or propylene oxide onto fatty alcohols, fatty acids, alkylphenols, glycerol mono- and diesters and sorbitan mono- and diesters of fatty acids or onto castoroil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example. Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Consistency Factors

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat®(BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol. Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Metal salts of fatty acids such as, for example, magnesium, aluminium and/or zinc stearate or ricinoleate may be used as stabilizers.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract, bambara nut extract, and vitamin complexes.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olarnin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-yl-methoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, filial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoflkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be produced by standard hot or cold processes.

EXAMPLES

Examples 1 and 2

Activity of OKG on the Metabolism of Hair Follicles

Human anagen hair follicles were isolated from scalp skin and transferred for cultivation in sterile 24 well plates using a modified Williams' Medium E. Cultivation took place for nine days, while the experimental treatment of the follicles started 24 hours from the beginning of the cultivation.

Hair follicles taken from a single donor were selected for the experiments after 18 h of cultivation. Only those follicles showing a good vital stage and a growth of not less than 0.2 mm have been considered suitable to be maintained in culture. 4 groups were prepared comprising 9 follicles, plated at the density of 3 hair follicles/plate. The following experiments were conducted to demonstrate the activity of OKG on hair follicle growth in concentrations of 0.005 to 0.01% b.w.—calculated on the total cultivation medium—compared to a control group. The activity of the OKG treatment is demonstrated by the increase of growth of the hair follicles expressed in [mm] which was determined every two days. The growth of the hair follicles was studied by microphotography and subsequently determined by image analysis. All the hair follicles were photographed every two days. The results are presented in Table 1:

TABLE 1

Growth of hair follicles - elongation in [mm] ± standard error

| | | Days of cultivation | | | | |
|---|---|---|---|---|---|---|
| Ex. | Sample | 1 | 3 | 5 | 7 | 9 |
| 0 | Control | 0 | 0.78 ± 0.035 | 1.42 ± 0.102 | 1.90 ± 0.138 | 2.23 ± 0.246 |
| 1 | OKG 0.01% b.w. | 0 | 0.88 ± 0.024 | 1.63 ± 0.067 | 2.25 ± 0.086 | 2.77 ± 0.163 |
| 2 | OKG 0.005% b.w. | 0 | 0.84 ± 0.022 | 1.50 ± 0.078 | 1.98 ± 0.155 | 2.35 ± 0.253 |

The results indicate that the addition of OKG leads to a significant increase in growth of the hair follicles.

Examples 3 and 4

Comparative Examples C1 to C4

Activity of OKG Compared to State of the Art Actives on the Metabolism of Hair Follicles In order to show the superiority of OKG compared to Ornithine on one hand and alpha-Ketoglutarate on the other, the influence of these compounds on the metabolism of hair follicles was studied under the conditions as explained in Examples 1 and 2. Table 2 shows the relative growth of hair follicles after 6 days of cultivation compared to a control sample. Examples 3 and 4 are according to the invention, examples C1-C4 are shown for comparison.

TABLE 2

Growth of hair follicles - elongation in [%] ± standard error

| Ex. | Sample | Conc. (% b.w.) | Number of hair follicles | Growth |
|---|---|---|---|---|
| 0 | Control | | 18 | 100 ± 2.9 |
| 3 | OKG | 0.001 | 12 | 112.7 ± 3.1 |
| 4 | OKG | 0.01 | 12 | 110.4 ± 4.0 |
| C1 | Ornithine | 0.001 | 12 | 105.1 ± 5.1 |
| C2 | Ornithine | 0.01 | 12 | 102.1 ± 5.0 |
| C3 | alpha-Ketoglutarate | 0.001 | 12 | 103.1 ± 3.1 |
| C4 | alpha-Ketoglutarate | 0.01 | 11 | 103.8 ± 3.8 |

The examples and comparative examples clearly indicate the superiority and synergistic effect of OKG on hair follicle stimulation compared to Ornithine and alpha-Ketoglutarate taken alone.

Example 5

Activity of OKG on the Decline of the Catagen Stage of Hair Follicles

The experiment according to Examples 1 and 2 was terminated after 9 days of cultivation. Subsequently, the hair follicles were subjected to a histological analysis by colouring with haematossilin and eosin in order to verify the morphological state of the dermopapilla. The results are shown in Table 3:

TABLE 3

Histological analysis of hair follicles

| Ex. | Sample | Anagen phase | Catagen phase |
|---|---|---|---|
| 0 | Control | 56% | 44% |
| 3 | OKG 0.1% b.w. | 78% | 22% |

The results indicate that the OKG treatment has significantly delayed the decline to the catagen phase of the hair follicles. Since growth of the hair follicles only takes place during the anagen phase the results also support the stimulating effects of OKG.

Example 6

Activity of OKG on the Number of Proliferative and Apoptotic Cells

After three days of cultivation samples were taken in order to determine the relative number of cells being in the proliferative or apoptotic state. The cells in apoptotic state were determined using an *Apoptag Fluorescein In-situ Apoptosis Detection Kit* (Chemicon International cod. S7110), while those in proliferative state were marked with the antibody Ki-67 (monoclonal mouse anti-human Ki-67, clone MIB1, Dako Cytomation cod. M7240). The total number of cells in the dermopapilla was analysed by marking their nuclei by means of DAPI (4', 6-diamidino-2-phenylindol dihydrochloride). The percentage of cells in the proliferative or apoptotic stage compared to the total number of cells was determined again by image analysis. The results are shown in Table 4.

TABLE 4

Number of cells in proliferative or apoptotic stage ± standard error

| Ex. | Sample | Proliferative stage | Apoptotic stage |
|---|---|---|---|
| 0 | Control | 10.74% ± 0.29 | 0.48% ± 0.105 |
| 4 | OKG 0.1% b.w. | 10.51% ± 0.17 | 0.17% ± 0.073 |

The results clearly indicate that the treatment of hair follicles with OKG significantly reduces the number of apoptotic cells.

The invention claimed is:

1. A method for treating disorders of hair follicles to prevent or inhibit hair loss and/or to promote hair growth and for treating skin diseases associated with disorders of hair follicles and hair growth, said method comprising administering an effective treating amount of ornithine alpha ketoglutarate (OKG) to a mammal.

2. A method for treating disorders of hair follicles to prevent or inhibit hair loss and/or to promote hair growth and for treating skin diseases associated with disorders of hair follicles and hair growth, said method comprising administering an effective treating amount of ornithine alpha ketoglutarate (OKG) and a toxicologically safe carrier selected from the group consisting of aliphatic alcohols having from 2 to 15 carbon atoms, polyols having from 2 to 15 carbon atoms, oil bodies and combinations thereof to a mammal.

3. A method for treating disorders of hair follicles to prevent or inhibit hair loss and/or to promote hair growth and for treating skin diseases associated with disorders of hair follicles and hair growth, said method comprising orally administering an effective treating amount of ornithine alpha ketoglutarate (OKG) and a toxicologically safe carrier selected from the group consisting of aliphatic alcohols having from 2 to 15 carbon atoms, polyols having from 2 to 15 carbon atoms, oil bodies and combinations thereof to a mammal.

4. A method for treating disorders of hair follicles to prevent or inhibit hair loss and/or to promote hair growth and for treating skin diseases associated with disorders of hair follicles and hair growth, said method comprising topically administering an effective treating amount of ornithine alpha ketoglutarate (OKG) and a toxicologically safe carrier selected from the group consisting of aliphatic alcohols having from 2 to 15 carbon atoms, polyols having from 2 to 15 carbon atoms, oil bodies and combinations thereof to the hair or skin of a mammal.

5. The method of claim 1 wherein said mammal is a human.
6. The method of claim 2 wherein said mammal is a human.
7. The method of claim 3 wherein said mammal is a human.

\* \* \* \* \*